United States Patent
Banholzer et al.

(10) Patent No.: US 6,506,900 B1
(45) Date of Patent: Jan. 14, 2003

(54) PROCESS FOR PREPARING A SCOPINE ESTER INTERMEDIATE

(75) Inventors: Rolf Banholzer, Stuttgart (DE); Manfred Graulich, Waldalgesheim (DE); Sven Luettke, Ockenheim (DE); Andreas Mathes, Ockenheim (DE); Helmut Meissner, Ingelheim (DE); Peter Specht, Ober-Hilbersheim (DE); Wolfgang Broeder, Heidesheim (DE)

(73) Assignee: Boehringer Ingelheim Pharma AG, Ingelheim (DE)

( * ) Notice: Subject to any disclaimer, the term of this patent is extended or adjusted under 35 U.S.C. 154(b) by 0 days.

(21) Appl. No.: 10/223,152

(22) Filed: Aug. 19, 2002

Related U.S. Application Data

(63) Continuation of application No. 10/025,425, filed on Dec. 19, 2001.
(60) Provisional application No. 60/265,443, filed on Jan. 31, 2001.

(51) Int. Cl.$^7$ .................. C07D 45/00; C07D 401/12
(52) U.S. Cl. ........................... 546/91; 546/125
(58) Field of Search .................. 546/91, 125

(56) References Cited

U.S. PATENT DOCUMENTS

| 5,610,163 A | | 3/1997 | Banholzer et al. |
| 5,770,738 A | * | 6/1998 | Banholzer et al. .......... 514/304 |

FOREIGN PATENT DOCUMENTS

| EP | 0 418 716 A1 | 3/1991 |

OTHER PUBLICATIONS

Petrovic, G. et al; "Synthesis of Acetyl Scopine. Intramolecular Reactions of N–Carbethoxy Nortropine–3alpha–benzenesulfenate"; Synlett 1999, No. 5, 635–637.

* cited by examiner

*Primary Examiner*—Joseph K. McKane
*Assistant Examiner*—Jennifer C. Murphy
(74) *Attorney, Agent, or Firm*—Robert P. Raymond; Philip I. Datlow; Alan R. Stempel

(57) ABSTRACT

The invention relates to a new process for preparing a scopine ester useful as an intermediate in preparing (1α,2β,4β,5α,7β)-7-[(hydroxydi-2-thienylacetyl)oxy]-9,9-dimethyl-3-oxa-9-azoniatricyclo[3.3.1.0$^{2,4}$] nonane-bromide.

14 Claims, No Drawings

PROCESS FOR PREPARING A SCOPINE ESTER INTERMEDIATE

RELATED APPLICATIONS

This application is a continuation of U.S. application Ser. No. 10/025,425, filed Dec. 19, 2001, which claims the benefit of U.S. Provisional Application Serial No. 60/265,443, filed on Jan. 31, 2001, and said applications are herein incorporated by reference in their entirety.

FIELD OF THE INVENTION

The invention relates to a new process for preparing a scopine ester useful as an intermediate in preparing (1α,2β,4β,5α,7β)-7-[(hydroxydi-2-thienylacetyl)oxy]-9,9-dimethyl-3-oxa-9-azoniatricyclo[3.3.1.0$^{2,4}$]nonane-bromide.

BACKGROUND OF THE INVENTION

The compound (1α,2β,4β,5α,7β)-7-[(hydroxydi-2-thienylacetyl)oxy]-9,9-dimethyl-3-oxa-9-azoniatricyclo[3.3.1.0$^{2,4}$]nonane-bromide is known from European Patent Application EP 418 716 A1 and has the following chemical structure:

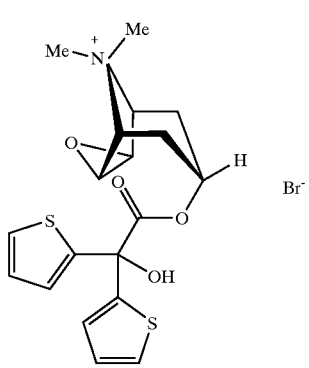

(I)

The compound has valuable pharmacological properties and is known by the name tiotropium bromide (BA679). Tiotropium bromide is a highly effective antichoinergic and can therefore provide therapeutic benefit in the treatment of asthma or COPD (chronic obstructive pulmonary disease).

Tiotropium bromide is preferably administered by inhalation. Suitable inhalable powders packed into appropriate capsules (inhalettes) may be used, which are administered using corresponding powder inhalers. Alternatively, it may be administered by the use of suitable inhalable aerosols. These also include powdered inhalable aerosols which contain, for example, HFA134a, HFA227 or mixtures thereof as propellant gas.

In view of its great efficacy, tiotropium bromide can be used in low therapeutic doses. On the one hand this imposes particular demands on the pharmaceutical production of the formulation to be used, and on the other hand it is particularly necessary to develop an industrial process for synthesising tiotropium bromide which ensures that the product is prepared not only in a good yield but also with exceptional purity.

European Patent Application EP 418 716 A1 discloses a method of synthesising tiotropium bromide. It corresponds to the method diagrammatically shown in Diagram 1.

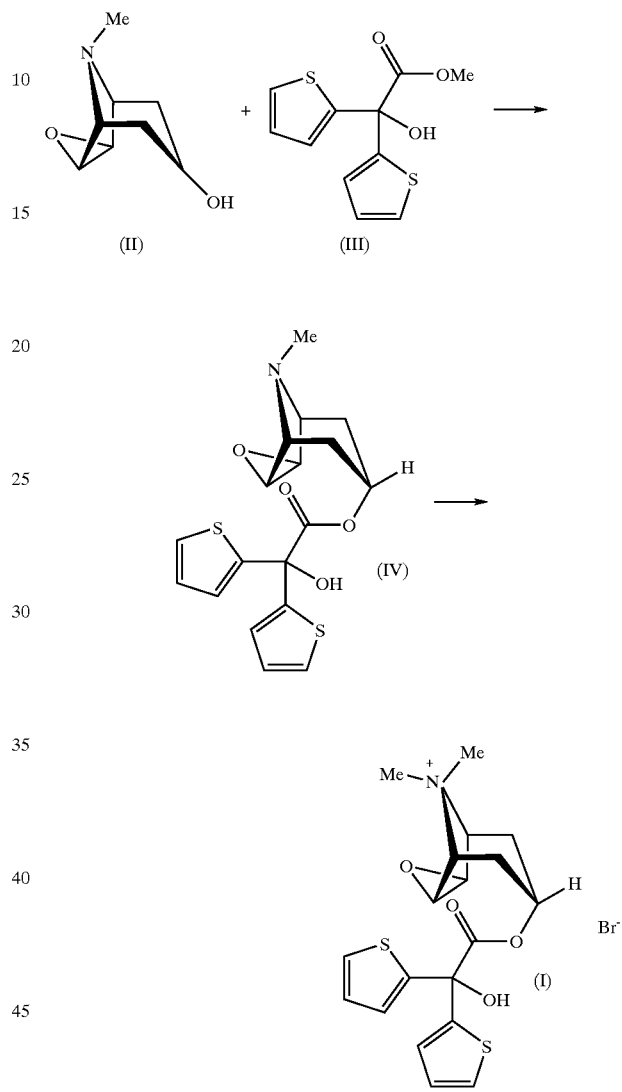

Diagram 1

In a first step, scopine (II) is reacted with methyl di-(2-thienyl)-glycolate-(III) to form di-(2-thienyl)-glycolic acid scopine ester (IV), which is then quaternized to form tiotropium bromide.

DETAILED DESCRIPTION OF THE INVENTION

It has been found that, surprisingly, tiotropium bromide can be obtained in much purer form if it is synthesised by a different method from that described in EP 418 716 A1. This alternative and surprisingly more advantageous method is diagrammatically illustrated in Diagram 2.

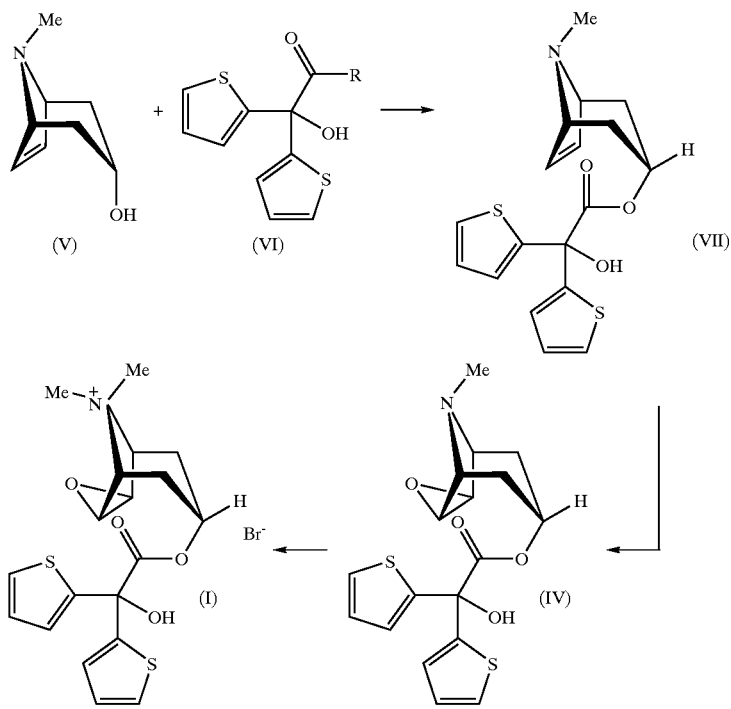

Diagram 2

Starting from the tropenol (V) known in the art and reacting with di-(2-thieny)-glycolic acid derivatives (VI), first the tropenol di-(2-thienyl)-glycolate (VII) is formed. This is converted into the corresponding scopine ester (IV) by epoxidation of the olefinic double bond.

Accordingly, the present invention relates to a process for preparing tiotropium bromide (I)

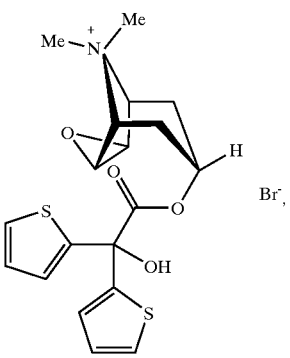

(I)

characterised in that the tropenol ester of formula (VII)

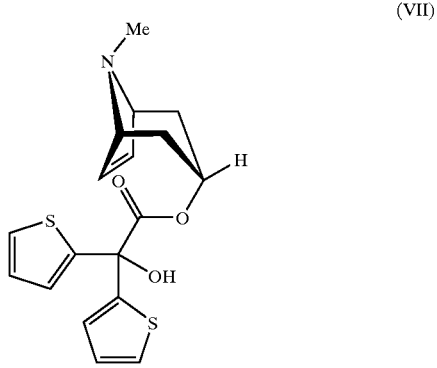

(VII)

is oxidised to form the scopine ester of formula (IV)

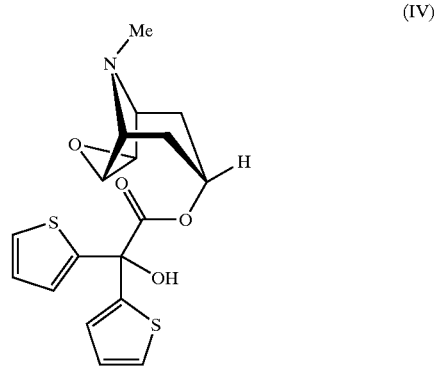

(IV)

which is then quaternized with methyl bromide to form tiotropium bromide (I).

Because of the central importance of the tropenol ester of formula (VII) according to the invention, in another aspect, the present invention relates generally to the use of the tropenol ester (VII), optionally in the form of the acid addition salts thereof, for preparing tiotropium bromide (I). In another aspect, the present invention relates to the use of the tropenol ester (VII), optionally in the form of the acid addition salts thereof, for preparing the scopine ester of formula (IV).

When tropenol ester (VII) is used in the form of an acid addition salt for preparing the scopine ester (IV), this acid addition salt is preferably selected from among hydrochloride, hydrobromide, hydrogen phosphate, hydrogen sulphate, tetrafluoroborate and hexafluorophosphate; the hydrochloride and hydrobromide are particularly preferred.

According to another aspect, the present invention relates to a process for preparing tiotropium bromide of formula (I)

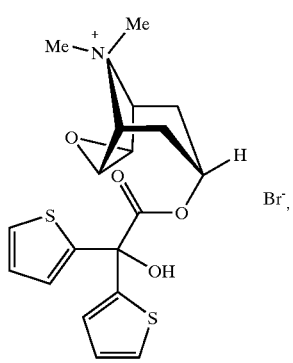

(I)

characterised in that in a first step tropenol of formula (V),

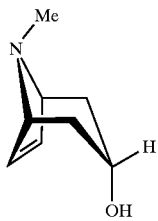

(V)

optionally in the form of the acid addition salts thereof, is reacted with an ester of formula (VI)

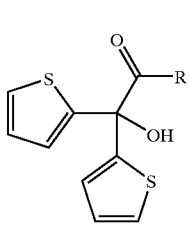

(VI)

wherein R denotes a group selected from among hydroxy, methoxy, ethoxy, O—N-succinimide, O—N-phthalimide, phenyloxy, nitrophenyloxy, fluorophenyloxy, pentafluorophenyloxy, vinyloxy, —S-methyl, —S-ethyl and —S-phenyl, to form the tropenol ester of formula (VII)

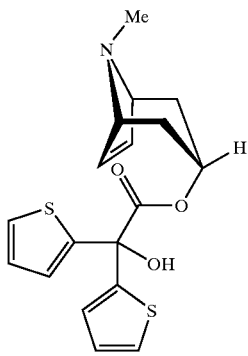

(VII)

which is then epoxidised in a second step to form the scopine ester of formula (IV)

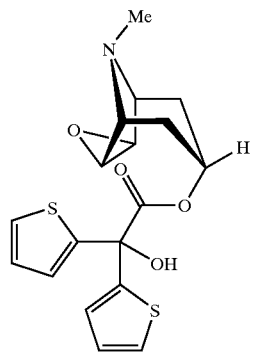

(IV)

and this is then quaternized in a third step using methylbromide to obtain tiotropium bromide (I).

Because of the central importance of the tropenol (V) as a starting material for preparing tiotropium bromide (I), in another aspect the present invention further relates to the use of tropenol (V), optionally in the form of the acid addition salts thereof, as a starting material for preparing tiotropium bromide (I).

To prepare the tropenol ester (VII), tropenol, optionally in the form of an acid addition salt thereof selected from among the hydrochloride, hydrobromide, hydrogen phosphate, hydrogen sulphate, tetrafluoroborate and hexafluorophosphate, preferably in the form of the hydrochloride or hydrobromide, most preferably in the form of the hydrochloride, is taken up in a suitable organic solvent, preferably in a solvent selected from among toluene, benzene, n-butylacetate, dichloromethane, THF, dioxane, dimethylacetamide, DMF and N-methylpyrrolidinone, preferably selected from among toluene, benzene, THF, dioxane, dimethylacetamide, DMF and N-methylpyrrolidinone, most preferably toluene or benzene, toluene being most particularly preferred as the solvent. According to the invention, 0.5–3 l, preferably 0.75–2.5 l, most preferably between 1.25 and 1.75 l of organic solvent are used per mol of tropenol (V) put in.

If tropenol is used in the form of an acid addition salt thereof, a base is added to the resulting mixture to liberate the tropenol. Suitable bases according to the invention are inorganic or organic bases, organic amines being particularly preferred. Organic amines which may be used include triethylamine, diisopropylethylamine, pyridine, dimethylaminopyridine, N-methylpyrrolidine, N-methylmorpholine or ammonia, the use of triethylamine, diisopropylethylamine, pyridine or ammonia being particularly preferred, while ammonia is most particularly preferred. At least 1 mol, preferably 1.25 to 2.5 mol, most preferably 1.5 to 2 mol of amine are added, per mol of tropenol salt used. The amine may be added at temperatures of between 0 and 60° C., preferably 15 to 50° C., most preferably 20 to 30° C. After the amine has been added, the suspension obtained is stirred at constant temperature for between 0.1 to 5 h, preferably between 0.5 to 2.5 h, most preferably between 0.75 and 1.5 h.

The ammonium salt thus obtained is filtered off and optionally washed with the organic solvent mentioned above. Between 0.1 and 1.5 l, preferably 0.3–1.0 l of solvent are used per mol of tropenol (V) put in.

Some of the solvent is distilled off in vacuo at elevated temperature, preferably at 30–80° C., most preferably at 40 to 60° C. The distillation temperature naturally depends on the choice of solvent used. Depending on the choice of solvent, the vacuum is adjusted so that distillation takes place in the temperature range specified above. Between 0.25 and 2 l, preferably 0.5–1.5 l of solvent are distilled off per mol of tropenol (V) put in. After the specified amount of solvent has been distilled off, the reaction solution is cooled to a temperature range of from 0–50° C., preferably to 15–35° C., and the di-(2-thienyl)glycolic acid derivative (VI) is added. Di-(2-thienyl)glycolic acid derivatives (VI) which may be used according to the invention are those compounds wherein R denotes hydroxy, methoxy, ethoxy, O—N-succinimide, O—N-phthalimide, phenyloxy, nitrophenyloxy, fluorophenyloxy, pentafluorophenyloxy, vinyloxy, —S-methyl, —S-ethyl or —S-phenyl. It is particularly preferred to use the compound (VI) wherein R denotes hydroxy, methoxy or ethoxy , most preferably methoxy or hydroxy. If the compound wherein R is hydroxy is used as the compound (VI), the reaction may be carried out in the presence of coupling reagents such as carbonyldiimidazole, carbonyldi-1,2,4-triazole, dicyclohexylcarbodiimide or ethyldimethylaminopropylcarbodiimide. Between 1 and 2 mol of compound (VI) are used per mol of tropenol (V) put in. Preferably, 1–1.5 mol of (VI) are used, and most preferably stoichiometric amounts of (VI) compared with (V) are used according to the invention. The reaction mixture obtained may optionally be heated to form a solution. A temperature in the range from 30–80° C., preferably from 40–60° C., most preferably about 45–55° C. is chosen.

The solution thus obtained is then added to another solution or mixture of an inorganic or organic base in one of the abovementioned solvents, preferably in the solvent which is used to prepare the mixture of (V) and (VI). Between 0.2 and 2.0 l, preferably 0.4–1.5 l, most preferably 0.5 to 1.0 l of solvent are used per mol of tropenol (V) put in, in order to prepare the solution or mixture containing a base. Where R equals methoxy, ethoxy, vinyloxy, phenyloxy, —S-methyl, —S-ethyl or —S-phenyl the reaction is carried out in the presence of an organic or inorganic base. The organic bases used are preferably organic amines, most preferably diisopropylethylamines, triethylamines, cyclic amines such as DBU or pyridine. Suitable inorganic bases are the alkali metal or alkaline earth metal carbonates, the alkoxides and hydrides of lithium, sodium, potassium, calcium such as sodium carbonate, lithium carbonate, potassium carbonate, calcium carbonate, sodium hydride, potassium hydride, calcium hydride, sodium methoxide, sodium ethoxide, potassium methoxide or potassium ethoxide. Most preferably, the inorganic base used is one of the abovementioned hydrides or alkoxides, preferably one of the abovementioned hydrides, the use of sodium hydride being particularly preferred according to the invention. At least stoichiometric amounts of base are used per mol of tropenol (V). Preferably, 1–3 mol, most preferably 1.25–2.5 mol, even more preferably 1.5 to 2 mol of base are used per mol of tropenol (V).

The solution of (V) and (VI) is combined with the base-containing solution or mixture described above, preferably over a period of 0.2–2.0 h, preferably over a period of 0.5 to 1.5 h. If an ester in which R denotes methoxy or ethoxy is used as the compound (VI), for example, it may be necessary to distil off the resulting alcohol at 40–90° C., preferably at 50 to 80° C., most preferably at 60–75° C. in vacuo, preferably at 150 to 500 mbar, most preferably at 200–350 mbar, particularly preferably at 250–300mbar. This procedure shifts the equilibrium of the reaction towards the tropenol ester (VII). Under these reaction conditions, some of the solvent is also distilled off. After the distillation is complete (about 5 to 10 h), the quantity of solvent distilled off can be added to the reaction solution if desired.

In any case, once distillation is complete, the solution obtained is cooled down again to a temperature range of below 40° C., preferably 0–35° C., most preferably 10–25° C. Hydrochloric acid is added to this mixture at constant temperature over a period of 0.2 to 2 h, preferably 0.4–0.6 h. The hydrochloric acid may be added either in the form of aqueous solutions or as a gas; the addition of aqueous solutions is preferred. Preferably, concentrated hydrochloric acid (36%) dissolved in water is added. Between 1 and 4 mol, preferably 1.5–3 mol, most preferably 2.0 to 2.5 mol HCl are preferably added per mol of tropenol (V) used. Preferably, 0.1–0.4 kg, most preferably 0.15–0.25 kg of 36% aqueous hydrochloric acid dissolved in 10–20 litres, preferably in 12–17 litres of water are added per mol of tropenol (V).

After everything has been added and the mixture has been thoroughly stirred the aqueous phase is separated off. It is then washed with a suitable water-immiscible organic solvent. The preferred solvent is a water-immiscible solvent selected from among methylene chloride and n-butylacetate, preferably methylene chloride. If desired, the first organic phase used to extract the aqueous phase is discarded and the extraction process is repeated once more.

The aqueous phase, optionally after previously being washed with one of the abovementioned water-immiscible solvents, is mixed once more with the water-immiscible solvent. Preferably 1–5 l, preferably 2–4 l, most preferably 2.5–3.5l of the water-immiscible solvent are used per mol of tropenol (V) originally put in. The mixture thus obtained is combined with an inorganic base, preferably selected from the alkali metal or alkaline earth metal carbonates of lithium, sodium, potassium, calcium such as, for example, sodium carbonate, lithium carbonate, potassium carbonate or calcium carbonate, sodium carbonate being particularly preferred, and thus adjusted to a pH of 7.5 to 11, preferably 8 to 10. The inorganic base is preferably added in the form of aqueous solutions. For example, according to the invention, it is particularly preferable to add 0.05 to 0.4 kg, preferably 0.1 to 0.2 kg of inorganic base dissolved in 0.25 to 1.5 l, preferably in 0.5 to 1 l, most preferably in 0.7 to 0.8 L of water per mol of tropenol (V) used.

After thorough mixing of the reaction mixture obtained, the aqueous phase is separated off and extracted one or more times with the water-immiscible solvent mentioned earlier. A total of 1–8 l, preferably 2–6 l, most preferably 3–5 l of the abovementioned water-immiscible solvent are used to extract the aqueous phase per mol of tropenol (V) originally used. The combined organic phases are subsequently freed from solvent by distillation at elevated temperature, preferably at 30–90° C., most preferably at 50–70° C. The temperature ranges specified above are highly dependent on the choice of solvent used, as will be apparent to anyone skilled in the art. If desired, a vacuum may also be applied for this distillative elimination of the solvent so as to keep the temperature within the temperature ranges defined hereinbefore. With solvents which are distilled off below the maximum temperature ranges defined above, the maximum distillation temperature will naturally be the boiling point of the solvent in question.

The residue remaining after distillation is taken up in an organic solvent. This solvent can be selected from among the solvents which may be used according to this specification to carry out the reaction of (V) and (VI) to form (VII). Preferably the same solvent is used as in this reaction. 1–5 l, preferably 1.5–4 l, preferably 2–3 l of solvent are used to dissolve the residue per mol of tropenol (V) originally used. The solution thus obtained is heated, to not more than the boiling temperature of the solvent, preferably to a range of from 50–100° C., most preferably 80–95° C. The heated solution is slowly cooled to a temperature in the range from −10° C. to 20° C., preferably 0–10° C. The tropenol ester (VII) is obtained in the form of colourless crystals which are separated off and dried. Drying is preferably carried out under inert gas at temperatures from 30–50° C.

The tropenol ester (VII) thus obtained is then epoxidised as described hereinafter to form the scopine ester (IV). A suitable solvent, preferably selected from among water, dimethylformamide, acetonitrile, dimethylacetamide and N-methylpyrrolidinone, most preferably dimethylformamide, is placed in a suitable reaction apparatus and heated to a temperature in the range from 30–70° C., preferably 40–60° C. 2–10 l, preferably 3–8 l, preferably 4–7 l, most preferably 5–6 l of solvent are used per mol of tropenol ester (VII) used. The tropenol ester (VII) is added to the solvent which has been heated as described above and the resulting mixture is stirred at constant temperature until a clear solution is obtained.

An epoxidising agent is then added batchwise to this solution at a temperature in the range from 20–50° C., preferably at 35–45° C. The preferred epoxidising agent is preferably vanadium pentoxide mixed with $H_2O_2$, most preferably an $H_2O_2$-urea complex in combination with vanadium pentoxide. Preferably, the hydrogen peroxide urea complex and vanadium pentoxide are added batchwise alternately, most preferably water is also added. 0.1–0.5 kg, preferably 0.15–0.3 kg of hydrogen peroxide-urea complex, 0.1–1.0 l, preferably 0.15–0.7 l, most preferably 0.2–0.4 l water as well as 0.001–0.1 kg, preferably 0.005–0.05 kg, most preferably 0.01–0.025 kg of vanadium pentoxide are used per mol of tropenol ester (VII) used. After everything has been added, the mixture is stirred for a period of 1–6 h, preferably 1.5–4 h, preferably 2–3 h at a temperature of 30–70° C. preferably 40–60° C., most preferably 45–55° C.

It is then cooled to a temperature in the range from 10–30° C., preferably to 15–25° C. and adjusted to a pH of 2.5–5.5, preferably a pH of 3.5–4.5 with hydrochloric acid. The hydrochloric acid may be added either in the form of aqueous solutions or as a gas, the addition of aqueous solutions being preferred. Preferably, concentrated hydrochloric acid (36%) dissolved in water is added. After thorough mixing, an inorganic salt is added, preferably sodium hydrogen sulphite. This is preferably added in the form of aqueous solutions. Most preferably, 20–100 g, preferably 30–80 g, most preferably 40–60 g of inorganic salt dissolved in 0.1–1 l, preferably 0.3–0.7 l of water (in each case per mol of compound (VII) used) are added per mol of tropenol ester (VII) used. Some of the solvent is distilled off at an internal temperature of 20–50° C., preferably 30–40° C. About 2–8 l, preferably 3–6 l of the solvent is eliminated per mol of compound put in. After cooling to about 15–25° C. Clarcel (Celite) is added (in an amount of about 40–100 g, preferably 60–80 g per mol of compound (VII) put in). By again adding hydrochloric acid, preferably dilute aqueous hydrochloric acid, a pH of 1–3, preferably 1.5–2.5 is obtained. Preferably, 10–30 g, preferably 15–20 g of 36% hydrochloric acid, dissolved in 5–15 l, preferably 8–12 l of water (per mol of (VII) put in) are used per mol of compound (VII) used.

The solution obtained is filtered and optionally extracted one, two or three times with a suitable, water-immiscible solvent. Preferably, a water-immiscible solvent selected from among methylene chloride and n-butylacetate, preferably methylene chloride, is used. The organic phases used to extract the aqueous phase are discarded.

The aqueous phase is mixed once again with the water-immiscible solvent, optionally after previous washing with one of the water-immiscible solvents mentioned above. Preferably, 1–5 l, preferably 2–4 l, most preferably 2.5–3.5 l of the water-immiscible solvent are used per mol of tropenol ester (VII) originally put in. The resulting mixture is combined with an inorganic base, preferably selected from the alkali metal or alkaline earth metal carbonates of lithium, sodium, potassium or calcium, such as, for example, sodium carbonate, lithium carbonate, potassium carbonate or calcium carbonate, sodium carbonate being particularly preferred, and adjusted to a pH of 8 to 11, preferably 9 to 10.5. The inorganic base is preferably added in the form of aqueous solutions. For example and according to the invention, most preferably, 0.05 to 0.4 kg, preferably 0.15 to 0.3 kg of sodium carbonate dissolved in 0.25 to 2 l, preferably in 0.75 to 1.25 l are added per mol of ester (VII) used.

After thorough mixing of the reaction mixture obtained, the aqueous phase is separated off and extracted one or more times with the water-immiscible solvent mentioned earlier. A total of 1–5 l, preferably 2–4 l of the abovementioned water-immiscible solvent are used to extract the aqueous phase per mol of tropenol ester (VII) originally used. The combined organic phases are subsequently freed from solvent by distillation at preferably 25–50° C., most preferably at 30–40° C. The temperature ranges specified above are highly dependent on the choice of solvent used, as will be apparent to anyone skilled in the art. If desired, a vacuum may also be applied for this distillative elimination of the solvent so as to keep the temperature within the temperature ranges defined hereinbefore. Preferably, distillation is carried out under a slight vacuum at 500–800 mbar, preferably at 600–700 mbar. About 2–6 l, preferably 3–5 l of the solvent is distilled off per mol of the ester (VII) originally put in.

It may possibly be necessary to eliminate impurities in the form of secondary amines at this point. This is done, according to the invention, by using organic carboxylic acid halides, preferably acid chlorides selected from among acetyl chloride, propionic acid chloride or butyric acid chloride. Acetyl chloride is preferably used. Usually, between 5 and 30 g, preferably 10–20 g of carboxylic acid halide are used per mol of ester (VII) originally used. After the addition of the carboxylic acid halide at 15–25° C. the mixture is stirred for 15 minutes to 1.5 h, preferably between 30 and 45 minutes at constant temperature.

Then the mixture is brought to a temperature in the range from 10–30° C., preferably to 15–25° C., and adjusted to a pH of 1–3, preferably a pH of 1.5–2.5 with hydrochloric acid. The hydrochloric acid may be added either in the form of aqueous solutions or as a gas; it is preferably added as an aqueous solution. Preferably, concentrated hydrochloric acid (36%) dissolved in water is added. Preferably, 0.05–0.5 kg, preferably 0.075–1.25kg of 36% hydrochloric acid, dissolved in 5–15 l, preferably 8–12 l of water (per mol of (VII) used) are used per mol of compound (VII) put in. The organic phase is separated off and discarded.

The aqueous phase is mixed once again with the water-immiscible solvent, optionally after previous washing with one of the water-immiscible solvents mentioned above. Preferably 1–5 l, preferably 2–4 l, most preferably 2.5–3.5 l of the water-immiscible solvent are used per mol of tropenol ester (VII) originally put in. The resulting mixture is combined with an inorganic base, preferably selected from the alkali metal or alkaline earth metal carbonates of lithium, sodium, potassium or calcium, such as, for example, sodium carbonate, lithium carbonate, potassium carbonate or calcium carbonate, sodium carbonate being particularly preferred, and adjusted to a pH of 8 to 11, preferably 9 to 10.5. The inorganic base is preferably added in the form of aqueous solutions. For example and according to the invention, most preferably, 0.05 to 0.4 kg, preferably 0.1 to 0.2 kg of sodium carbonate dissolved in 0.25 to 2 l, preferably in 0.7 to 1.2 l are added per mol of ester (VII) used.

After thorough mixing of the reaction mixture obtained, the aqueous phase is separated off and extracted once or preferably twice with the water-immiscible solvent mentioned earlier. A total of 0.5–2.5 l, preferably 1–2 l of the abovementioned water-immiscible solvent are used to extract the aqueous phase per mol of tropenol ester (VII) originally used. The combined organic phases are subsequently freed from solvent by distillation at preferably 25–50° C., most preferably at 30–40° C. (about 1–3 l, preferably 1.5–2.5 solvent are eliminated per mol of ester (VII) used). A solvent selected from among dimethylformamide, dimethylacetamide, N-methylpyrrolidinone or dichloromethane, preferably dimethylformamide, is then added. Between 1 and 5 kg, preferably between 1.5 and 4 kg, most preferably between 2 and 3 kg of solvent are used per mol of ester (VII) put in. The remaining traces of the water-immiscible solvent used previously for extraction are distilled off from this solution under a slight vacuum (600–700 mbar) and at a temperature of 30–40° C. The solution of scopine ester (IV) thus obtained is used directly in the next step without any further isolation of the intermediate compound.

In order to prepare tiotropium bromide (I), methyl bromide is introduced into the scopine ester solution obtainable according to the instructions provided hereinbefore at 10–30° C., preferably at 15–25° C. As a solution of scopine ester (IV) is used in this step without any measurement of the yield of the preceding step, the quantities specified below relate to the tropenol ester (VII) originally put in. At least 1 mol of methylbromide is used per mol of scopine ester (IV). 0.1–0.2 kg, preferably 0.11–0.15 kg of methylbromide are preferably used according to the invention per mol of tropenol ester (VII) used. After all the methylbromide has been added the mixture is stirred at 15–35° C. for 1–3 days, preferably for 48–72 hours. Then the solvent dimethylformamide is partly distilled off in vacuo at 30–60° C., preferably at 45–55° C. The vacuum is selected so that the solvent is distilled off within the temperature ranges mentioned above. About 0.5–2.0 l, preferably 1.0–1.75 l of solvent are distilled off per mol of tropenol ester (VII) used and then cooled to about 5–20° C., preferably 10–15° C. At this temperature, the mixture is stirred until the crude product has fully crystallised and the crystals precipitated are separated off and dried at 30–50° C. under inert gas, preferably nitrogen.

The product may be further purified by crystallisation from methanol. About 2–8 l, preferably 3–7 l, most preferably 4–5 l of methanol are used per 1 mol of tiotropium bromide (I) and the mixture thus obtained is refluxed until the product dissolves. It is then cooled to 0–1 5° C., preferably 3–7° C. and the product crystallises with stirring. After total crystallisation, the crystals are separated off and finally dried at 30–50° C. under an inert gas, preferably nitrogen.

The product thus obtained may optionally be converted into its monohydrate. To do this, the following method may be used.

In a reaction vessel of suitable size the solvent is mixed with tiotropium bromide. 0.4 to 1.5 kg, preferably 0.6 to 1 kg, most preferably about 0.8 kg of water are used as solvent per mol of tiotropium bromide used. The resulting mixture is heated with stirring, preferably to more than 50° C., most preferably to more than 60° C. The maximum temperature which can be used is determined by the boiling point of the water used as solvent. Preferably the mixture is heated to a range of 80–90° C.

Activated charcoal, dry or moistened with water, is added to this solution. Preferably, 10 to 50 g, most preferably 15 to 35 g, particularly preferably 25 g of activated charcoal are used per mol of tiotropium bromide put in. If desired, the activated charcoal may be suspended in water before being added to the solution containing tiotropium bromide. 70 to 200 g, preferably 100 to 160 g, most preferably about 135 g of water are used per mol of tiotropium bromide put in, in order to suspend the activated charcoal. If the activated charcoal is suspended in water before being added to the solution containing tiotropium bromide, it is advisable to rinse with the same amount of water.

Stirring is continued for between 5 and 60 minutes, preferably between 10 and 30 minutes, most preferably about 15 minutes at constant temperature after the addition of the activated charcoal and the resulting mixture is filtered to eliminate the activated charcoal. The filter is then rinsed with water. This is done using 140 to 400 g, preferably 200 to 320 g, most preferably about 270 g of water per mol of tiotropium bromide used. The filtrate is then slowly cooled, preferably to a temperature of 20–25° C. Cooling is preferably carried out at a cooling rate of 1 to 10° C. per 10 to 30 minutes, preferably 2 to 8° C. per 10 to 30 minutes, most preferably 3 to 5° C. per 10 to 20 minutes, particularly preferably 3 to 5° C. per 20 minutes approximately. If desired, the cooling to 20 to 25° C. may be followed by further cooling to below 20° C., most preferably to 10 to 15° C. After the cooling has taken place, the mixture is stirred for between 20 minutes and 3 hours, preferably between 40 minutes and 2 hours, most preferably about one hour, in order to complete the crystallisation.

Finally, the crystals formed are isolated by filtering or suction filtering of the solvent. If it proves necessary to subject the crystals obtained to another washing step, it is advisable to use water or acetone as washing solvent. 0.1 to 1.0 l, preferably 0.2 to 0.5 l, most preferably about 0.3 l of solvent may be used per mol of tiotropium bromide used in order to wash the tiotropium bromide monohydrate crystals obtained. If desired, the washing step may be repeated.

The product obtained is dried in vacuo or using circulating hot air to achieve a water content of 2.5–4.0%.

The Examples which follow serve to illustrate some methods of synthesis carried out by way of example in order to prepare tiotropium bromide. They are intended to be taken as possible methods provided by way of example, without limiting the invention to their content.

Preparation of the Tropenol Ester (VII)

Ammonia (1.8 kg) is added to 10.9 kg of tropenol hydrochloride in toluene (95 l) at 25° C. The suspension obtained is stirred at constant temperature for about 1 h. The ammonium hydrochloride formed is then filtered off and rinsed with toluene (26 l). At an external temperature of about 50° C. some of the toluene (about 60 l) is distilled off in vacuo. After cooling to about 25° C., 15.8 kg of methyl di-(2-thienyl)glycolate is added and the resulting mixture is heated to 50° C. to dissolve it. Toluene (40 l) is placed in another apparatus and sodium hydride (2.7 kg) is added thereto at about 25° C. The solution previously prepared from tropenol and methyl glycolate is added to this solution within 1 hour at 30° C. After it has all been added the mixture is heated to 75° C. at reduced pressure for about 7 hours with stirring. The methanol formed is distilled off. The mixture remaining is cooled and added to a mixture of water (958 l) and 36% hydrochloric acid (13.2 kg). The aqueous phase is then separated off and washed with methylene chloride (56l). After the addition of some more methylene chloride (198 l) the mixture thus obtained is adjusted to pH=9 with prepared soda solution (9.6 kg of soda in 45 l of water). The methylene chloride phase is separated off and the aqueous phase is stirred with methylene chloride (262 L). The methylene chloride phase is evaporated down to the residue at 65° C. The residue is taken up in toluene (166 l) and heated to 95° C. The toluene solution is cooled to 0° C. The crystals obtained are separated off, washed with toluene (33 l) and dried at about 50° C. for a maximum of 24 hours in a nitrogen current.

Yield: 18.6 kg (83%); melting point: about 160° C. (measured by DSC at a heating rate of 10 K/min);

Preparation of the Scopine Ester (IV)

260 l DMF are placed in a suitable reaction apparatus and heated to 50° C. Then 16.2 kg of tropenol ester (VII) are added and the mixture is stirred until a clear solution is obtained. After cooling to 40° C., hydrogen peroxide-urea complex (10.2 kg), water (13 l) and vanadium-(V)-oxide (0.7 kg) are added successively and in batches and the contents of the apparatus are heated to about 50° C. After 2–3 h stirring at constant temperature the mixture is cooled to about 20° C. The reaction mixture obtained is adjusted to a pH of about 4.0 with hydrochloric acid (36%). Prepared sodium bisulphite solution (2.4 kg in 24 l of water) is added. At an internal temperature of 35° C. the solvent is partly distilled off in vacuo (about 210 l). The mixture is cooled to about 20° C. again and Clarcel (3.2 kg) is added. The resulting mixture is adjusted to a pH of about 2.0 with dilute hydrochloric acid (36%, 0.8 kg in about 440 l of water). The solution obtained is filtered and extracted with methylene chloride (58 l). The methylene chloride phase is discarded. Methylene chloride (130 l) is again added to the aqueous phase and a pH of about 10.0 is obtained using a prepared soda solution (11.0 kg in 51 l of water). The methylene chloride phase is separated off and the aqueous phase is extracted with methylene chloride (136 l). Methylene chloride (about 175 l) is distilled off from the combined methylene chloride phases in a slight vacuum (600–700 mbar) at 40° C. The contents of the apparatus are cooled to 20° C., acetyl chloride (about 0.5 kg) is added and the mixture is stirred for about 40 minutes at 20° C. The reaction solution is transferred into a second apparatus. The pH is adjusted to 2.0 with a prepared hydrochloric acid solution (4.7 kg of hydrochloric acid, 36% strength in 460 l water) at 20° C. The methylene chloride phase is separated off and discarded. The aqueous phase is washed with methylene chloride (39 l). Then methylene chloride (130 l) is added and a pH of 10.0 is obtained with a prepared soda solution (7.8 kg of soda in 38 l water) at 20° C. After 15 minutes' stirring the organic phase is separated off and the aqueous phase is washed twice with methylene chloride (97 l and 65 l). The methylene chloride phases are combined and some of the methylene chloride (90 l) is distilled off in a slight vacuum at a temperature of 30–40° C. Then dimethylformamide (114 kg) is added and the remaining methylene chloride is distilled off in vacuo at 40° C. The contents of the apparatus are cooled to 20° C.

Preparation of the Tiotropium Bromide (I)

Methyl bromide (5.1 kg) is added to the scopine ester solution obtained according to the procedure described above at 20° C. The contents of the apparatus are stirred at 30° C. for about 2.5 days. At 50° C., 70 l of DMF are distilled off in vacuo. The solution is transferred into a smaller apparatus. It is rinsed with DMF (10 l). More DMF is distilled off at 50° C. in vacuo until a total of about 100 l of distillate is obtained. It is cooled to 15° C. and stirred for another 2 hours at this temperature. The product is isolated using suction dryers, then washed with cold DMF (10 l) at 15° C. and cold acetone (25 l) at 15° C. It is dried at a maximum temperature of 50° C. for not more than 36 hours in a nitrogen current.

Yield: 13.2 kg (88%); melting point: 200–230° C. (depending on the purity of the crude product);

The crude product thus obtained (10.3 kg) is added to methanol (66 l). The mixture is refluxed to dissolve it. The solution is cooled to 7° C. and stirred for 1.5 h at this temperature. The product is isolated using suction dryers, washed with cold methanol (11 l) at 7° C. and dried for max. 36 h at about 50° C. in a nitrogen current.

Yield: 9.9 kg (96%); melting point: 228° C. (determined by DSC at a heating rate of 10 K/min).

If desired, the product thus obtained can be converted into the crystalline monohydrate of tiotropium bromide. This can be done as follows.

15.0 kg of tiotropium bromide are added to 25.7 kg of water in a suitable reaction vessel. The mixture is heated to 80–90° C. and stirred at constant temperature until a clear solution is formed. Activated charcoal (0.8 kg), moistened with water, is suspended in 4.4 kg of water, this mixture is added to the solution containing tiotropium bromide and rinsed with 4.3 kg of water. The mixture thus obtained is stirred for at least 15 min at 80–90° C. and then filtered through a heated filter into an apparatus which has been preheated to an outer temperature of 70° C. The filter is rinsed with 8.6 kg of water. The contents of the apparatus are cooled to a temperature of 20–25° C. at a rate of 3–5° C. per 20 minutes. The apparatus is further cooled to 10–15° C. using cold water and the crystallisation is completed by stirring for at least one hour. The crystals are isolated using a suction drier, the isolated crystal slurry is washed with 9 l of cold water (10–15° C.) and cold acetone (10–15° C.). The crystals obtained are dried at about 25° C. over about 2 hours in a nitrogen current.

Yield: 13.4 kg of tiotropium bromide monohydrate (86% of theory)

Melting point: 230° C. (determined by DSC at a heating rate of 10 K/min).

We claim:

1. A process for preparing the scopine ester of formula (IV):

(IV)

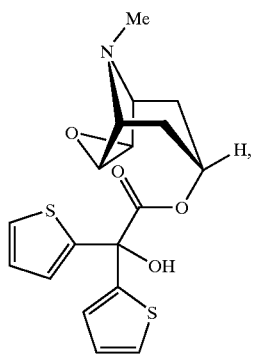

said process comprising epoxidizing the tropenol ester of formula (VII):

(VII)

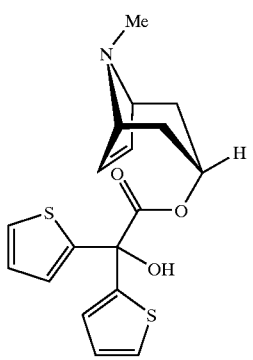

to form the scopine ester of formula (IV).

2. A process according to claim 1, wherein a mixture of vanadium pentoxide with hydrogen peroxide is used as the epoxidising agent for epoxidising (VII) to form (IV).

3. A process according to claim 1, wherein the epoxidation of (VII) to form (IV) is carried out in a solvent which is selected from among water, dimethylformamide, acetonitrile, dimethylacetamide and N-methylpyrrolidinone.

4. A process according to any one of claims 1 to 3, wherein the compound of formula (VII):

(VII)

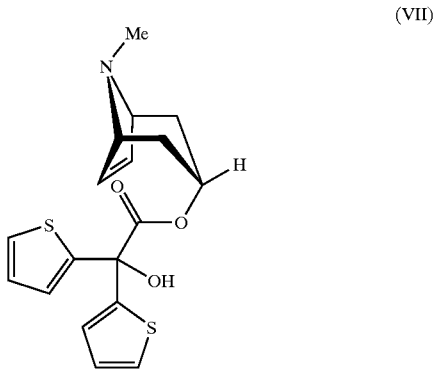

is obtained by reacting tropenol of formula (V), (V)

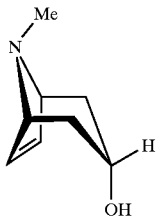

optionally in the form of an acid addition salt thereof, with an ester of formula (VI)

(VI)

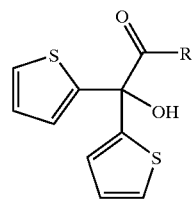

wherein R is a group which is selected from among hydroxy, methoxy, ethoxy, O—N-succinimide, O—N-phthalimide, phenyloxy, nitrophenyloxy, fluorophenyloxy, pentafluorophenyloxy, vinyloxy, —S-methyl, —S-ethyl and —S-phenyl.

5. A process according to claim 4, wherein the tropenol (V) is used in the form of an acid addition salt thereof which is selected from among the hydrochloride, hydrobromide, hydrogen phosphate, hydrogen sulphate, tetrafluoroborate and hexafluorophosphate salts.

6. A process according to claim 4, wherein the reaction of (V) with (VI) to form (VII) is carried out in a suitable organic solvent.

7. A process according to claim 4, wherein the reaction of (V) with (VI) to form (VII) is carried out in an organic solvent selected from among toluene, benzene, n-butylacetate, dichloromethane, THF, dioxane, dimethylacetamide, DMF and N-methylpyrrolidinone.

8. A process according to claim 4, wherein the reaction of (V) with (VI) to form (VII) is carried out in the presence of an organic or inorganic base.

9. A process according to claim 4, wherein the reaction of (V) with (VI) to form (VII) is carried out in the presence of a base selected from among the organic amines.

10. A process according to claim 4, wherein the reaction of (V) with (VI) to form (VII) is carried out in the presence of diisopropylethylamine, triethylamine, DBU or pyridine.

11. A process according to claim 4, wherein the reaction of (V) with (VI) to form (VII) is carried out in the presence an inorganic base.

12. A process according to claim 4, wherein the reaction of (V) with (VI) to form (VII) is carried out in the presence of an alkali metal or alkaline earth metal carbonate, alkoxide or hydride of lithium, sodium, potassium or calcium.

13. A process according to claim 4, wherein if R denotes hydroxy in the compound of formula (VI), the reaction of (V) with (VI) to form (VII) is carried out in the presence of coupling reagents.

14. A process according to claim 13, wherein the coupling reagents are selected from among carbonyldiimidazole, carbonyldi-1,2,4-triazole, dicyclohexylcarbodiimide and ethyl-dimethylaminopropylcarbodiimide.

* * * * *

UNITED STATES PATENT AND TRADEMARK OFFICE
CERTIFICATE OF CORRECTION

PATENT NO. : 6,506,900 B1
DATED : January 14, 2003
INVENTOR(S) : Rolf Banholzer et al.

It is certified that error appears in the above-identified patent and that said Letters Patent is hereby corrected as shown below:

<u>Title page,</u>
Item [73], Assignee, please correct name of Assignee by deleting "Boehringer Ingelheim Pharma AG" and inserting -- Boehringer Ingelheim Pharma KG --.

Signed and Sealed this

Thirteenth Day of May, 2003

JAMES E. ROGAN
*Director of the United States Patent and Trademark Office*